United States Patent
Miller et al.

(10) Patent No.: US 11,911,351 B2
(45) Date of Patent: Feb. 27, 2024

(54) METHODS FOR TREATING SLEEP APNEA WITH COMBINATIONS OF ATOMOXETINE AND (R)-OXYBUTYNIN

(71) Applicant: Apnimed, Inc. (Delaware), Cambridge, MA (US)

(72) Inventors: Lawrence G. Miller, Cambridge, MA (US); Barry Wohl, Cambridge, MA (US); Walter J. Lunsmann, Harvard, MA (US)

(73) Assignee: APNIMED, INC. (DELAWARE), Cambridge, MA (US)

( * ) Notice: Subject to any disclaimer, the term of this patent is extended or adjusted under 35 U.S.C. 154(b) by 620 days.

(21) Appl. No.: 16/965,960

(22) PCT Filed: Jan. 30, 2019

(86) PCT No.: PCT/US2019/015781
§ 371 (c)(1),
(2) Date: Jul. 29, 2020

(87) PCT Pub. No.: WO2019/152475
PCT Pub. Date: Aug. 8, 2019

(65) Prior Publication Data
US 2021/0038541 A1    Feb. 11, 2021

Related U.S. Application Data

(60) Provisional application No. 62/623,892, filed on Jan. 30, 2018.

(51) Int. Cl.
*A61K 31/138*    (2006.01)
*A61K 31/216*    (2006.01)
(Continued)

(52) U.S. Cl.
CPC .......... *A61K 31/138* (2013.01); *A61K 31/216* (2013.01); *A61P 11/00* (2018.01); *A61K 45/06* (2013.01)

(58) Field of Classification Search
CPC ...... A61K 31/138; A61K 31/216; A61P 11/00
See application file for complete search history.

(56) References Cited

U.S. PATENT DOCUMENTS

| 5,968,932 A | 10/1999 | Winokur et al. |
| 11,123,313 B2 | 9/2021 | Wellman et al. |

(Continued)

FOREIGN PATENT DOCUMENTS

| CN | 1396829 A | 2/2003 |
| CN | 101132777 A | 2/2008 |

(Continued)

OTHER PUBLICATIONS

ClinicalTrials.gov; NCT02908529; Atomexetine and Oxybutynin in Obstructive Sleep Aponea (ATOSA); Sep. 16, 2016 Version; https://clinicaltrials.gov/ct2/history/NCT02908529?V_1=View#StudyPageTop; accesses Dec. 5, 2022 (Year: 2016).*

(Continued)

*Primary Examiner* — Timothy P Thomas
(74) *Attorney, Agent, or Firm* — Honigman LLP

(57) ABSTRACT

In general, the invention relates to pharmaceutical compositions comprising (R)-oxybutynin and a norepinephrine reuptake inhibitor (NRI) and methods of treating Sleep Apnea comprising administering (R)-oxybutynin and a norepinephrine reuptake inhibitor (NRI). In some embodiments, the NRI is atomoxetine.

25 Claims, 1 Drawing Sheet

(51) Int. Cl.
  *A61P 11/00* (2006.01)
  *A61K 45/06* (2006.01)

(56) References Cited

U.S. PATENT DOCUMENTS

| | | | |
|---|---|---|---|
| 2002/0010216 | A1 | 1/2002 | Rogosky et al. |
| 2002/0155113 | A1 | 10/2002 | Chun et al. |
| 2003/0060513 | A1 | 3/2003 | Arneric et al. |
| 2005/0192268 | A1 | 9/2005 | Ek et al. |
| 2006/0039866 | A1 | 2/2006 | Rao et al. |
| 2006/0039867 | A1 | 2/2006 | Rao et al. |
| 2007/0021920 | A1 | 1/2007 | Ishikawa et al. |
| 2008/0009538 | A1 | 1/2008 | Skolnick |
| 2008/0181943 | A1 | 7/2008 | Cuine et al. |
| 2009/0169620 | A1 | 7/2009 | Venkatesh et al. |
| 2010/0029770 | A1 | 2/2010 | Roberts et al. |
| 2010/0204058 | A1 | 8/2010 | Chang et al. |
| 2011/0253133 | A1 | 10/2011 | Martin et al. |
| 2013/0189319 | A1 | 7/2013 | Cook et al. |
| 2014/0323423 | A1 | 10/2014 | Dipierro et al. |
| 2018/0296565 | A1 | 10/2018 | Hsu |
| 2020/0054583 | A1* | 2/2020 | Wellman .............. A61K 31/216 |
| 2022/0096401 | A1 | 3/2022 | Montemurro et al. |

FOREIGN PATENT DOCUMENTS

| | | | |
|---|---|---|---|
| CN | 103458899 | A | 12/2013 |
| GB | 940540 | | 10/1963 |
| JP | 2003523382 | A | 8/2003 |
| JP | 2012176958 | A | 9/2012 |
| WO | 0162236 | A2 | 8/2001 |
| WO | 03039436 | A2 | 5/2003 |
| WO | 2004060366 | A1 | 7/2004 |
| WO | 2004096141 | A2 | 11/2004 |
| WO | 2006055854 | A2 | 5/2006 |
| WO | 2006069030 | A1 | 6/2006 |
| WO | 2006113448 | A1 | 10/2006 |
| WO | 2008122019 | A1 | 10/2008 |
| WO | 2008124128 | A2 | 10/2008 |
| WO | 2009023820 | A1 | 2/2009 |
| WO | 2011123815 | A1 | 10/2011 |
| WO | 2014138162 | A1 | 9/2014 |
| WO | 2016062285 | A1 | 4/2016 |
| WO | 2016176177 | A1 | 11/2016 |
| WO | 2017031319 | A1 | 2/2017 |
| WO | 2018200775 | A1 | 11/2018 |
| WO | 2019152474 | A1 | 8/2019 |
| WO | 2020163785 | A1 | 8/2020 |

OTHER PUBLICATIONS

Smith et al.; "Comparison of the antimuscarinic and antispasmodic actions of racemic oxybutynin and desethyloxybutynin and their enantiomers with those of racemic terodiline"; 1998; Arneimittelforschung; 48(10): 1012-8; PubMed abstract; PMID: 9825119 (Year: 1998).*
PCT/2019/015781 International Search Report dated May 13, 2019.
ClinicalTrials.gov, Atomoxetine and oxybutynin in Obstructive Sleep Apnea, NCT02908529, Jan. 19, 2018; URL:https://clinicaltrials.gov/ct2/history/NCT02908529?A=3&B=3&C=merged#StudyPageTop.
Sangal, Bart R., et al; Atomoxetine Improves Sleepiness and Gloval Servity of Illness but not the Respirtary Disturbance Index in Mild to Moderate obstructive Sllep Apnea with Sleepiness; Sleep Medicine, Elsevier; vol. 9, No. 5, pp. 506-510 Jul. 1, 2008.
Taranto-Montemurro, Luigi, et al.; the Combination of Atomoxetine and Oxybutynin Greatly reduces obstructive Sleep Apnea Severity: A Randomized, Placebo-Controlled, Double-Blind Crossover Trial; Am Jour of Respiratory and Critical Care Medicine, Am Thoracic Society, pp. 1-45, Nov. 5, 2018.
Wuest, Melinda, Oxybutynin, xPharm: The Comprehensive Pharmacology Reference, pp. 1-13, Elsevier Inc., Dec. 31, 2008.

Alza Corp., Ditropan (oxybutynin chloride) Tablets and Syrup & Extended Release Tablets, retrieved from the internet: URL:https://www.accessdata.fda.gov/drugsatfda_docs/label/2008/017577s034,018211s017,020897s018lbl.pdf [rtrieved on Dec. 7, 2022] Feb. 1, 2008.
Anonymous, Wikipedia, Oxybutynin, retrieved from the internet: URL:https://en.wikipedia.org/w/index.php?title=Oxybutynin&oldid=822003676 [retrieved on Dec. 7, 2022], Jan. 23, 2018.
Kachur, J.F. et al., R and S Enantiomers of Oxybutynin: Pharmacological Effects in Guinea Pig Bladder and intestine, The J of Pharmacology and Experimental Therapeutics, vol. 247, No. 3, pp. 867-872, The Am Society for Pharmacology and Experimental Therapeutics, Aug. 12, 1988.
Norohna-Blob, L., et al., Enantiomers of Oxybutynin: In Vitro Pharmaceological Characterization at M1, M2 and M3 Muscarinic Receptors and in Vivo Effects on Urinary Bladder Contraction, Mydriasis and Salivary secretion in Guinea Pigs, The J of Pharmaceology and Experimental Therapeutics, vol. 256, No. 2, pp. 562-567, 1991.
Ali, I., et al., Enantiomeric Separation and Simulation Studies of Pheniramine, Oxybutynin, Cetirizine, and Brinzolamide Chiral Drugs on Amylose-Based Columns Chirality vol. 26, No. 3, pp. 136-143, Wiley Periodicals, Inc., Jan. 26, 2014.
Barnes, Muscarinic Receptor Subtypes in Airways, Life Sciences, Jan. 1, 1993, 52(5-6):521-7.
Barnes, PJ (1998) Muscarinic receptor subtypes in airways, Research in Immunology, 149(3) 201-202.
Basner, et al., Phasic electromyographic activity of the genioglossus increases in normals durig slow-wave sleep, respir. Physiol., Feb. 1991, 83(2):189-200.
Berry , et al., Rules for scoring respiratory events in sleep: update of the 2007 aasm manual for the scoring of sleep and associated events. Deliberations of the sleep apnea definitions task force of the Am Academy of Sleep Medicine, J. Clin. Sleep Med., Oct. 2012, 8(5):597-619.
Berry, et al., Acute effects of paroxetine on genioglossus activity in obstructin sleep apnea; Sleep, Dec. 1999, 22(8):1087-1092.
Brooks, et al., Obstructive sleep apnea as a cause of systemic hypertension; evidence from a canine model; J. Clin. Invest., Jan. 1997, 99(1):106-109.
Brownell, et al., Protriptyline in obstruction sleep apnea: a double-blind trial; N. Engl. J. Med., Oct. 1982, 3007(17):1037-1042.
Buchanan, et al., 5-HT2A receptor activation is necessary for Co2-induced arousal, J Neurophysiol, Jul. 2015, 114(1);233-243.
Carbrry, et al., Role of common hypnotics on the phenotypic causes of obstructive sleep apnoea: paradoxical effexts of zolpidem, Eur Respir J., 2017, 50:1701344, 11 pgs.
Carberry, et al., The effects of zolpidem in obstructive sleep apnea—an open-label pilot study, J Sleep Res., Apr. 2019, 28:312853, 5 pgs.
Carter, et al., High dose zopiclone does not change osa severity, the respiratory arousal threshold, genioflossus muscle respnsiveness or next-day sleepiness and alertness in selecged peole with OSA, Presented in the form of Abstract at World Sleep 2019, Vancouver, Canada, 2019; Sleep Med., Dec. 2019, 64(Suppl.):S56, 1 pg.
Carter, et al., effect of 1 month of zopiclone on obsturctive sleep apnoea severity and symptoms: a randomised controled trail, Eur Respir J., Jul. 2018, 52(1):1800149, 12 pgs.
Carter, et al., Zopiclone increases the arousal threshold without impairing genioglossus activity in obstructive sleep apnea, Sleep, Apr. 2016, 39(4):757-766.
Chan, et al., Endogenous excitatory drive modulating respiratory muscle activity across sleep-wake states; Am. J of Respiratory & Critical Care Medicine, Dec. 2006, 174(11):1264-1273.
Clark, et al., Sleep apnea: treatment with protriptyline, Neurology, Sep. 1979, 29(9pt1):1278-1292.
Cohn, et al., An update on the use of transdermal oxybutynin in the management of overactive bladder disorer, Ther Adv Urol., Apr. 2016, 8(2):83-90.
Conway, et al., Protriptyline in the tratment of sleep apnoea, Thorax, Jan. 1982, 37(1):49-53.
Drugbank Accession No. DB00245, Benzatropine, Jun. 13, 2005, 1 page.

(56) References Cited

OTHER PUBLICATIONS

Drugbank Accession No. DB00782, Propantheline, Jun. 13, 2005, 1 page.
Drugbank Accession No. DB01062, Oxybutynin, Jun. 13, 2005, 1 page.
Drugbank Accession No. DB08897, Aclidinium, Jun. 4, 2013, 1 page.
Drugbank Accession No. DB09185, Viloaxine, Oct. 16, 2015, 1 page.
Eckert, et al., Defining phenotypic causes of obstruction leep apnea; identification of novel therapeutic targets, Am. J. Respir Crit. Care Med., Oct. 2013, 188(8):995-1004.
Eckert, et al., Trazodone increases the arousal threshold in obstructive sleep apnea patients with a low arousal threshold, Sleep, Apr. 2014, 37(4):811-819.
Eckert, et al., "Eszopiclone Increases the Respiratory Arousal Threshold and Lowers the apnoea/hypopnoea Index in Obstructive Sleep Apnoea Patients With a Low Arousal Threshold," Clin. Sci. (Lond)., Jun. 2011, 120(12):505-514.
Edwards, et al., "Acetazolamide improves loop gain but not the other physiological traits causing obstructive sleep apnea," J. Physiol., Mar. 2012, 590(Pt 5):1199-1211.
Engleman, et al., "Improving CPAP use by patients with the sleep apnoea/hypopnoea syndrome (SAHS)," Sleep Med. Rev., Feb. 2003, 7(1):81-99.
European Application No. 18791670.5 Extended European Search Report dated Jan. 25, 2021.
European Application No. 20752195.6 Extended European Search Report dated Oct. 10, 2022.
fda.gov [online], FDA approves first generic Strattera for the treatment of ADHA, May 30, 2017, retrieved Sep. 24, 2020 from URL ,https://www.fda.gov/news-events/press-announcements/fda-approves-first-generic-strattera-treatment-adha., 1 page.
Fenik, et al., "REM sleep-like atonia of hypoglossal (XII) motoneurons is caused by loss of noradrenergic and serotonergic inputs," Am. J. Respir. Crit. Care. Med., Nov. 2005, 172(10):1322-1330.
Findley, et al., "Automobile accidents involving patients with obstructive sleep apnea," Am. Rev. Respir. Dis., Aug. 1988, 138(2):337-340.
Foldvary-Schaefer, et al., Gabapentin increases slow-wave sleep in normal adults, Epilepsia, Dec. 2002, 43(12):1493-1497.
Georgia 15226/01 Search Report dated Dec. 21, 2020.
Grace, et al., "Identification of the mechanism mediating genioglossus muscle suppression in REM sleep," Am. J. Respir. Crit. Care. Med., Feb. 2013, 187(3):311-319.
Grace, et al., "K+ channel modulation causes genioglossus inhibition in REM sleep and is a strategy for reactivation," Respir. Physiol. Neurobiol., Sep. 2013, 188(3):277-288.
Hanzel, et al., "Response of Obstructive Sleep Apnea to Fluoxetine and Protriptyline," Chest, Aug. 1991, 100(2):416-21.
Heinzer, et al., Trazodone increases arousal threshold in obstructive sleep apnoea, Eur Respir J, Jun. 2008, 31(6):1308-1312.
Hodges, et al., Defects in breathing and thermoregulation in mice with near-complete absence of central serotonin neurons, j Neurosci, Mar. 2008, 28(10):2495-2505.
Hoffstein, "Blood pressure, snoring, obesity, and nocturnal hypoxaemia," Lancet, Sep. 1994, 344(8923):643-645.
Horner, et al., State-dependent and reflex drives to the upper airway: basic physiology with clinical implications, J Apl Physio, Feb. 2014, 116(3):325-336.
Horner, R.L. (2001) The neuropharmaceology of upper airway motor control in the awake and asleep states: implications for obstructive sleep apnoea, Respir. Res 2, 286.
Hung, et al., "Association of sleep apnoea with myocardial infarction in men," Lancet, Aug. 1990, 336(8710):261-264.
Kraiczi, et al., "Effect of serotonin uptake inhibition on breathing during sleep and daytime symptoms in obstructive sleep apnea," Sleep, Jan. 1999, 22(1):61-67.

Kribbs, et al., "Objective measurement of patterns of nasal CPAP use by patients with obstructive sleep apnea," The American Review of Respiratory Disease, Apr. 1993, 147:887-895.
Kubin, et al., Neural Control of the Upper Airway: Respiratory and State-Dependent Mechanisms, Compr Physiol, Sep. 2016, 6(4):1801-1850.
Kubin, et al., "Control of Upper Airway Motoneurons During REM Sleep," Apr. 1998, News Physiol. Sci., 13(2):91-97.
Lai, et al., "Changes in monoamine release in the ventral horn and hypoglossal nucleus linked to pontine inhibition of muscle tone: An in vivo microdialysis study," J Neurosci., 21(8):7384-7391.
Lim, et al., 0067 Reboxetine and hyoscine butylbromide reduce obstructive sleep apnoea severty, Abstract, presented at Sleep Down Under 2019 31st ASM or Australasian Sleep Association and the Australasian Sleep Technologists Assoc, Sydney, Australia, Oct. 16-19, 2019; j Sleep Res, Oct. 2019, 28(suppl. 1);p. 31, 1 pg.
Lim, et al., Reboxetine and hyoscine butylbromide improve upper airway function during nonrapid eye movement and suppress rapid eye movement sleep in healthy individials, Sleep, Apr. 2019, 42(4):zsy261, 10 pgs.
Marshall, et al., "Two Randomized Placebo-Controlled Trials to Evaluate the Efficacy and Tolerability of Mirtazapine for the Treatment of Obstructive Sleep Apnea," Sleep, Jun. 2008, 31(6):824-831.
Matthews, et al., Selective noradrenalinereuptake inhibitors for schizophrenia, Cochrane Database of Systematic Reviews, Jan. 2018, (1), 129 pages.
Nicholas, et al., Discharge patterns of human tensor palatini motor units during sleep onset, Sleep, May 2012, 35(5):699-707.
Nieto, et al., "Association of sleep-disordered breathing, sleep apnea, and hypertension in a large community-based study," Sleep heart health study, JAMA, Apr. 2000, 283(14):1829-183.
PCT/US2018/029518 International Preliminary Report on Patentability dated Oct. 29, 2019, 10 pages; and International Search Report & Written Opinion dated Aug. 21, 2018.
PCT/US2020/017323 International Preliminary Report on Patentability dated Aug. 10, 2021, 8 pages.
PCT/US2020/017323 International Search Report & Written Opinion dated Jun. 26, 2020, 12 pgs.
Peppard, et al., "Increased Prevalence of Sleep-Disordered Breathing in Adults," Am. J. Epidemiol., May 2013, 177(9):1006-1014.
Peppard, et al., "Prospective study of the association between sleep-disordered breathing and hypertension," The New England Journal of Medicine, May 2000, 342(19):1378-1384.
Perger, E., et al., Reboxetine plus Oxybutynin for Obstructed Sleep Apnea Treatment, B014 Pathophysiology, CV Disease, and Covid What's Happening in Sleep Research Right Now Mini Synmposium, Am J Respir Crit Care Med 2021;203;A1101 Abstract.
Rao, et al., Gabapentin augments whole blood serotonin in healthy young men, j Neural Transm, 1988, 73(2):129-134.
Ratnavadivel; et al., Marked reduction in obstructive sleep panea severity in slow wave sleep j Clin Sleep Med, Dec. 2009, 5(6):519-524.
Redline, et al., "Neuropsychological function in mild sleep-disordered breathing," Sleep, Feb. 1997, 20(2):160-167.
Ruehland, et al., "The new AASM criteria for scoring hypopneas: Impact on the apnea hypopnea index," Sleep, Feb. 2009, 32(2):150-157.
Sands, et al., Enhanced Upper-airway Muscle Responsiveness is a Distinct Feature of Overweight/Obese Individuals without Sleep Apnea, Am j Respir Crit Care Med, Oct. 2014, 190(8):930-937.
Sands, et al., Phenotyping pharyngeal pathophysiology using polysomnography in patients with obstructive sleep apnea, Am j Respir Crit Care Med, May 2018, 1979(9):1187-1197.
Sands, et al., Quantifying the arousal threshold using polysomnography in obstructive sleep apnea, Sleep, Jan. 2018, 4191):zsx183, 9 pages.
Shahar, et al., "Sleep-disordered breathing and cardiovascular disease: Cross-sectional results of the sleep heart health study," Am. J. Respir. Crit. Care Med., Jan. 2001, 163(1):19-25.
Smales, et al., Trazodone Effects on Obstructive Sleep Apnea and Non-REM Arousal Threshold, Ann Am Thorac Soc, May 2015, 12(5):758-764.
Smith, et al., The effects of protriptyline in sleep-disordered breathing, Am Rev Respir Dis, 1983; 127(1):8-13.

(56) References Cited

OTHER PUBLICATIONS

Somers, et al., "Sympathetic neural mechanisms in obstructive sleep apnea," J. Clin. Invest., Oct. 1995, 96(4):1897-1904.
Song, et al., Alpha2-adrenergic blockage rescues hypoglossal motor defense against obstructive sleep apnea, JCI Insight, Feb. 2017, 2:391456, 16 pages.
Sood, et al., "Genioglossus muscle activity and serotonergic modulation of hypoglossal motor output in obese Zucker rats," J. Appl. Physiol., Jun. 2007, 102(6):2240-2250.
Sood, et al., "Inhibition of serotonergic medullary raphe obscurus neurons suppresses genioglossus and diaphragm activities in anesthetized but not conscious rats," J. Appl. Physiol., Jun. 2006, 100:1807-1821.
Sood, et al., "Role of endogenous serotonin in modulating genioglossus muscle activity in awake an sleeping rats," American Journal of Respiratory and Critical Care Medicine, Nov. 2005.
Sullivan, S.S., et al., Emerging drugs for common conditions of sleepiness: obstructive sleep apnea and narcolepsy; Expert Opinion on Emerging Drugs, 20(4), 571-582; 2015.
Taranto-Montemurro, et al., Desipramine improves upper airway collapsibility and reduces OSA severity in patients with minimal muscle compensation, Eur Respir J, Oct. 2016, 48:1340-1350.
Taranto-Montemurro, et al., Neural memory of the genioglossus muscle during sleep is stage-dependent in healthy subjects and obstructive sleep apnoea patients, The J of Physiology, Jul. 2018, 593(21):5163-5173.
Taranto-Montemurro, et al., Targeting Endotypic Traits with Medications for the Pharmacological Treatment of Obstructive Sleep Apnea. A Review of the Current Literature, J Clin Med, Nov. 2019, 8(11):1846.
Taranto-Montemurro, et al., "Effects of Tiagabine on Slow Wave Sleep and Arousal Threshold in Patients With Obstructive Sleep Apnea," Sleep, Feb. 2017, 40(2):zsw047, 7 pages.
Taranto-Montemurro, Luigi, et al., Desipramine Increases Genioglossus Activity and Reduces Upper Airway Collapsibility during Non-REM Sleep in Healthy Subjects; American Journal of Respiratory and Critical Care Medicine, vol. 194, No. 7, Oct. 1, 2016, pp. 878-885 (possibly XP055529037).
Thornton, Sleep aids and sedatives, JACEP, Sep. 1977, 6(9):408-412.
Veasey, S., et al., Obstructive Sleep Apnea Pharmacotherapy, Am J of Respiratory & Critical Care medicine, 187(3), 226-227.
Weaver & Gurnstein., "Adherence to Continuous Positive Airway Pressure Therapy: The Challenge to Effective Treatment," Proc. Am. Thorac. Soc., Feb. 2008, 5(2):173-178.
Weerts, et al., restricted sedation and absence of cognitive impairments after administration of intranasal scopolamine, j Psychopharmacolo, Aug. 2015, 29(12):1231-1235.
Weiner, et al., 5-Hydroxytryptamine2A Receptor inverse Agonists as Antipsychotics, The J of Pharmaceoboy & Experimental Therapeutics, Oct. 2001, 299(1):268-276.
Wellman, et al., "A method for measuring and modeling the physiological traits causing obstructive sleep apnea," J. Appl. Physiol., Jun. 2011, 110(6):1627-1637.
Wellman, et al., "A simplified method for determining phenotypic traits in patients with obstructive sleep apnea," J. Appl. Physiol., Apr. 2013, 114(7):911-922.
Wellman, et al., "Effect of oxygen in obstructive sleep apnea: Role of loop gain," Respir. Physiol. Neurobiol., Jul. 2008, 162(2):144-151.
Wessendorf, et al., "Sleep-disordered breathing among patients with first-ever stroke," J. Neurol., Jan. 2000, 247(1):41-47.
White, et al., The antagonisms of atropine to the eeg effects of adrenergic drugs, J Pharmacol Exp Ther, Apr. 1959, 125(4):339-346.
Whyte, et al., Role of Protriptyline and acetazolamide in the sleep apnea/hypopnea syndrome, Sleep, Oct. 1988, 11(5):463-472.
Wilkinson, et al., Discharge patterns of human genioglossus motor units during sleep onset, Sleep, Apr. 2008, 31(4):525-533.
Yokoyama, et al., Once-daily oxybutynin patch iproves nocturia and sleep quality in Japanese patients with overactive bladder: post-hoc analysis of a phase III randomized clinical trial, In J Urol, Mar. 2015, 22:684-688.
Younes, "Contributions of upper airway mechanics and control mechanisms to severity of obstructive apnea," Am. J. Respir. Crit. Care Med., Sep. 2003, 168(6):645-658.
Young, et al., "Burden of Sleep Apnea: Rationale, Design, and Major Findings of the Wisconsin Sleep Cohort Study," WMJ, Aug. 2009, 108(5):246-249.
Young, et al., "Epidemiology of obstructive sleep apnea: a population health perspective," Am. J. Respir. Crit. Care. Med., May 2002;, 165(9):1217-1239.

* cited by examiner

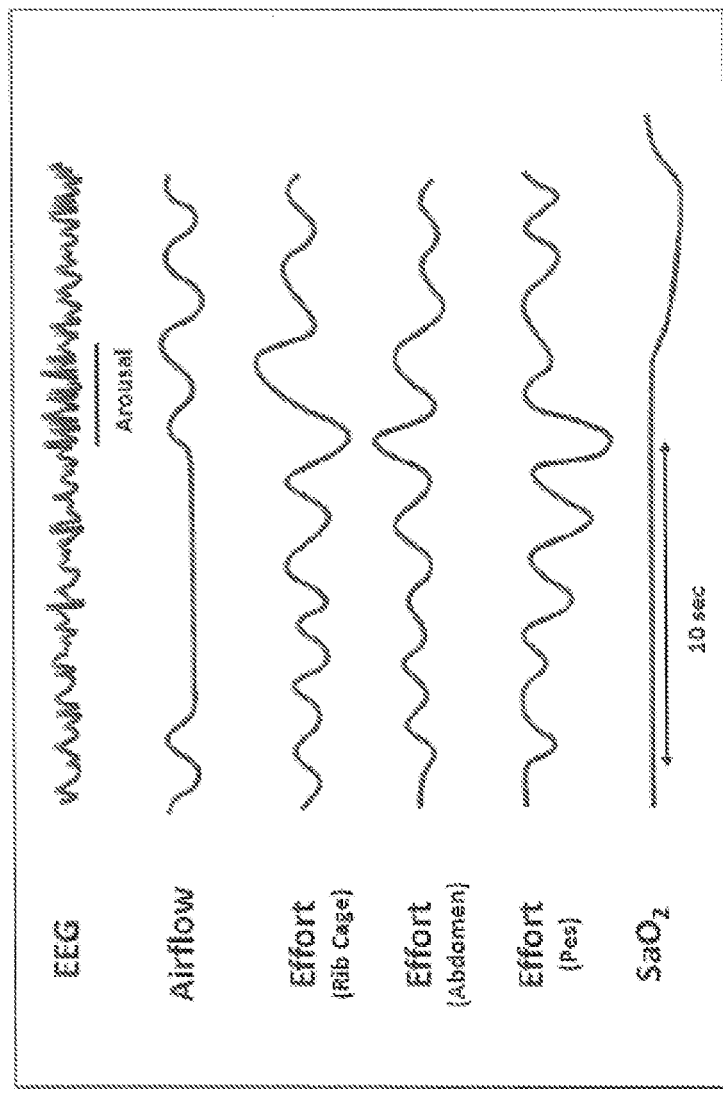

METHODS FOR TREATING SLEEP APNEA WITH COMBINATIONS OF ATOMOXETINE AND (R)-OXYBUTYNIN

CROSS-REFERENCE TO RELATED APPLICATIONS

This application is a National Stage Application and claims priority under 35 U.S.C. § 371 to Patent Cooperation Treaty application PCT/US2019/015781, filed Jan. 30, 2019, which claims the benefit of and priority under 35 U.S.C. § 119(e) to U.S. Provisional Application No. 62/623,892, filed Jan. 30, 2018. Priority is claimed to both of these applications and the disclosures of these prior applications are considered part of the disclosure of this application, and to the extent allowed, the entire contents of the aforementioned applications are incorporated herein.

TECHNICAL FIELD

The present invention provides pharmaceutical compositions comprising (R)-oxybutynin and a norepinephrine reuptake inhibitor (NRI) and methods of treating Sleep Apnea comprising administering (R)-oxybutynin and a norepinephrine reuptake inhibitor (NRI).

BACKGROUND

Obstructive Sleep Apnea (OSA) is a common disorder caused by collapse of the pharyngeal airway during sleep. OSA can have serious health consequences.

SUMMARY

One aspect of the present invention provides a method of treating a subject having a condition associated with pharyngeal airway collapse, the method comprising administering to a subject in need thereof an effective amount of (i) a norepinephrine reuptake inhibitor (NRI) and (ii) substantially enantiomerically pure (R)-oxybutynin.

Embodiments of this aspect of the invention may include one or more of the following optional features. In some embodiments, the NRI is a norepinephrine selective reuptake inhibitor (NSRI). In some embodiments, the NSRI is selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine. In some embodiments, the NRI is a norepinephrine non-selective reuptake inhibitor (NNRI) selected from the group consisting of Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Protryptyline, Radafaxine, Tapentadol, Teniloxazine, and Venlafaxine. In some embodiments, the NRI is selected from the group consisting of Atomoxetine and Reboxetine. In some embodiments, the NRI is Atomoxetine. In some embodiments, the Atomoxetine is administered at a dosage of from about 20 to about 100 mg (e.g., about 25 to about 75 mg). In some embodiments, the (R)-oxybutynin is in an immediate release formulation. In some embodiments, the (R)-oxybutynin is in an extended release formulation. In some embodiments, the (R)-oxybutynin is administered at a dosage of from about 2 to about 15 mg. For example, the (R)-oxybutynin may be in an immediate release formulation and administered at a dosage of from about 2.5 to about 10 mg. Or for example, the (R)-oxybutynin may be in an extended release formulation and may be administered at a dosage of from about 5 to about 15 mg. In some embodiments, the condition associated with pharyngeal airway collapse is Sleep Apnea or Simple Snoring. For example, the condition associated with pharyngeal airway collapse may be Obstructive Sleep Apnea (OSA). In some embodiments, the subject is in a non-fully conscious state (e.g., sleep). In some embodiments, the NRI and (R)-oxybutynin are administered in a single composition. In some embodiments, the single composition is an oral administration form (e.g., a syrup, pill, tablet, troche, capsule, or patch).

Another aspect of the invention provides a pharmaceutical composition comprising (i) a norepinephrine reuptake inhibitor (NRI) and (ii) substantially enantiomerically pure (R)-oxybutynin, in a pharmaceutically acceptable carrier.

Embodiments of this aspect of the invention may include one or more of the following optional features. In some embodiments, the NRI is a norepinephrine selective reuptake inhibitor (NSRI). In some embodiments, the NSRI is selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine. In some embodiments, NRI is a norepinephrine non-selective reuptake inhibitor (NNRI) selected from the group consisting of Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Protryptyline, Radafaxine, Tapentadol, Teniloxazine, and Venlafaxine. In some embodiments, the NRI is selected from the group consisting of Atomoxetine and Reboxetine. In some embodiments, the NRI is Atomoxetine. In some embodiments, the Atomoxetine is present in an amount of from about 20 to about 100 mg (e.g., about 25 to about 75 mg). In some embodiments, the (R)-oxybutynin is in an immediate release formulation. In some embodiments, the (R)-oxybutynin is in an extended release formulation. In some embodiments, the (R)-oxybutynin is present in an amount of from about 2 to about 15 mg. For example, the (R)-oxybutynin may be in an immediate release formulation and may be present in an amount of from about 2.5 to about 10 mg. Or for example, the (R)-oxybutynin may be in an extended release formulation and may be present in an amount of from about 5 to about 15 mg. In some embodiments, the composition is for use in treating a subject having a condition associated with pharyngeal airway collapse. In some embodiments, the condition associated with pharyngeal airway collapse is Sleep Apnea or Simple Snoring. In some embodiments, the condition associated with pharyngeal airway collapse is Obstructive Sleep Apnea (OSA). In some embodiments, the subject is in a non-fully conscious state (e.g., sleep).

Another aspect of the invention provides a norepinephrine reuptake inhibitor (NRI) and substantially enantiomerically pure (R)-oxybutynin for use in treating a subject having a condition associated with pharyngeal airway collapse.

Another aspect of the invention provides a kit comprising a norepinephrine reuptake inhibitor (NRI) and substantially enantiomerically pure (R)-oxybutynin. In some embodiments, the kit is for use in treating a subject having a condition associated with pharyngeal airway collapse.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

BRIEF DESCRIPTION OF THE DRAWINGS

The following FIGURES are provided by way of example and are not intended to limit the scope of the claimed invention.

FIG. 1. Graphic illustration of an obstructive apnea. The top channel shows the electroencephalogram (EEG) pattern of sleep. The next channel represents airflow. The next three channels show ventilatory effort by movements of the rib cage and abdomen and changes in esophageal pressure, all of which reflect contraction of respiratory muscles. The last channel indicates oxyhemoglobin saturation.

DETAILED DESCRIPTION

In humans, the pharyngeal airway region has no bone or cartilage support, and it is held open by muscles. When these muscles relax during sleep, the pharynx can collapse resulting in cessation of airflow. As shown in FIG. 1, ventilatory effort continues and increases in an attempt to overcome the obstruction, shown by an increase in esophageal pressure change. Rib cage and abdominal movements are in the opposite direction as a result of the diaphragm contracting against an occluded airway, forcing the abdominal wall to distend out and the chest wall to cave inward.

Increasing efforts to breathe lead to an arousal from sleep, visualisable on an EEG (FIG. 1), and result in opening of the airway and a resumption of normal breathing. The lack of airflow during the apnea also causes hypoxia, shown by a drop in oxyhemoglobin saturation (FIG. 1). Severity is generally measured using the apnea-hypopnea index (AHI), which is the combined average number of apneas (cessation of breathing for at least ten seconds) and hypopneas (reduced airflow and oxygen saturation) that occur per hour of sleep (Ruehland et al., The new AASM criteria for scoring hypopneas: Impact on the apnea hypopnea index. SLEEP 2009; 32(2):150-157).

When astringent definition of OSA is used (an AHI of >15 events per hour or AHI>5 events per hour with daytime sleepiness), the estimated prevalence is approximately 15 percent in males and 5 percent in females. An estimated 30 million individuals in the United States have OSA, of which approximately 6 million have been diagnosed. The prevalence of OSA in the United States appears to be increasing due to aging and increasing rates of obesity. OSA is associated with major comorbidities and economic costs, including: hypertension, diabetes, cardiovascular disease, motor vehicle accidents, workplace accidents, and fatigue/lost productivity. (Young et al., WMJ 2009; 108:246; Peppard et al., Am J Epidemiol 2013; 177:1006.)

The present leading treatment is continuous positive airway pressure (CPAP). CPAP is effective in virtually all patients, and approximately 85% of diagnosed patients are prescribed CPAP, but compliance is low. Patients find CPAP uncomfortable and often intolerable; at least 30% of patients (up to 80%) are regularly non-adherent and thus untreated (Weaver, Proc Am Thorac Soc. 2008 Feb. 15; 5(2): 173-178). Other treatment modalities with variable rates of success include oral appliances (10%) and surgery (5%), but neither is likely to be effective across the general population. No pharmacologic treatments have been shown to be effective to date.

The search for medicines to activate pharyngeal muscles in sleeping humans has been discouraging; agents such as serotonin reuptake inhibitors, tricyclic antidepressants, and sedatives have all been tested in humans and shown to be ineffective at reducing OSA severity. See, e.g., Proia and Hudgel, Chest. 1991 August; 100(2):416-21; Brownell et al., N Engl J Med 1982, 307:1037-1042; Sangal et al., Sleep Med. 2008 July; 9(5):506-10. Epub 2007 Sep. 27; Marshall et al. p. 2008 June; 31(6):824-31; Eckert et al., Clin Sci (Lond). 2011 June; 120(12); 505-14; Taranto-Montemurro et al., Sleep. 2017 Feb. 1; 40(2).

Methods of Treatment

The methods described herein include methods for the treatment of disorders associated with pharyngeal airway muscle collapse during sleep. In some embodiments, the disorder is Obstructive Sleep Apnea (OSA) or Simple Snoring. Generally, the methods include administering a therapeutically effective amount of a norepinephrine reuptake inhibitor and substantially enantomerically pure (R)-oxybutynin as known in the art and/or described herein, to a subject who is in need of, or who has been determined to be in need of, such treatment.

As used in this context, to "treat" means to ameliorate at least one symptom of the disorder associated with pharyngeal airway collapse. Often, pharyngeal airway collapse during sleep results in snoring and/or an interruption in breathing (apnea or hypopnea), arousal from sleep, and reduced oxygenation (hypoxemia); thus, a treatment can result in a reduction in snoring, apneas/hypopneas, sleep fragmentation, and hypoxemia. Administration of a therapeutically effective amount of a compound described herein for the treatment of a subject with OSA will result in decreased AHI.

An effective amount can be administered in one or more administrations, applications or dosages. The compositions can be administered from one or more times per day to one or more times per week; including once every other day. In some embodiments, the compositions are administered daily. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds (i.e., NRI and (R)-oxybutynin, in a single composition or in separate compositions) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In some embodiments, the methods include administering a dose of 20-100 mg atomoxetine (or a dose equivalent thereof of another NRI) and a dose of 2-15 mg (R)-oxybutynin. In some embodiments, the methods include administering 75 mg atomoxetine/6 mg (R)-oxybutynin; 75 mg atomoxetine/5 mg (R)-oxybutynin; 75 mg atomoxetine/4.5 mg (R)-oxybutynin; 50 mg atomoxetine/4 mg (R)-oxybutynin; or 25 mg atomoxetine/3 mg (R)-oxybutynin, e.g., 15-60, e.g., 15-25, 20-30, or 20-45 minutes before sleep time.

Pharmaceutical Compositions and Methods of Administration

The methods described herein include the use of pharmaceutical compositions comprising a norepinephrine reuptake inhibitor and substantially enantiomerically pure (R)-oxybutynin as active ingredients. The norepinephrine reuptake inhibitor and (R)-oxybutynin can be administered in a single composition or in separate compositions.

Exemplary norepinephrine reuptake inhibitors (NRIs) include the selective NRIs Amedalin (UK-3540-1), Atomoxetine (Strattera), CP-39,332, Daledalin (UK-3557-15), Edivoxetine (LY-2216684), Esreboxetine, Lortalamine (LM-1404), Nisoxetine (LY-94,939), Reboxetine (Edronax, Vestra), Talopram (Lu 3-010), Talsupram (Lu 5-005), Tandamine (AY-23,946), Viloxazine (Vivalan); non-selective NRIs include Amitriptiline, Amoxapine, Bupropion, Ciclazindol, Desipramine, Desvenlafaxine, Dexmethylphenidate, Diethylpropion, Doxepin, Duloxetine, Imipramine, Levomilnacipran, Manifaxine (GW-320,659), Maprotiline, Methylphenidate, Milnacipran, Nefazodone, Nortriptyline, Phendimetrazine, Phenmetrazine, Protryptyline, Radafaxine (GW-353,162), Tapentadol (Nucynta), Teniloxazine (Lucelan, Metatone) and Venlafaxine.

In some embodiments, the norepinephrine reuptake inhibitor is atomoxetine.

(R)-oxybutynin is an antimuscarinic drug. It is the (R)-enantiomer of oxybutynin. A composition comprising substantially enantiomerically pure (R)-oxybutynin, as described herein, comprises an enantiomeric excess of (R)-oxybutynin relative to its enantiomeric pair (i.e., (S)-oxybutynin). The enantiomeric excess of the substantially enantiomerically pure (R)-oxybutynin may be ≥80%, ≥90%, ≥95%, ≥98%, ≥99%, ≥99.5%, ≥99.8% or ≥99.9%.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., hypnotics including zolpidem, eszopiclone, benzodiazepines, gabapentin, tiagabine, and xyrem. In some embodiments, patients having OSA have a low arousal threshold, which can be exacerbated by the administered norepinephrine inhibitor. In such embodiments where patients have a low arousal threshold caused or worsened by the use of one or more norepinephrine inhibitors (e.g., atomoxetine), a hypnotic can be used as a supplementary active compound to increase the arousal threshold of the patient having OSA, pharyngeal airway collapse, or a combination thereof. In some embodiments, the arousal threshold of a patient can be measured by polysomnography (PSG). In some embodiments, a pharmaceutical composition comprises one or more norepinephrine reuptake inhibitors, substantially enantiomerically pure (R)-oxybutynin, and a hypnotic. In some embodiments, a method is provided for treating a subject having a condition associated with pharyngeal airway collapse, the method comprising administering to a subject in need thereof an effective amount of (i) a norepinephrine reuptake inhibitor (NRI); (ii) substantially enantomerically pure (R)-oxybutynin; and (iii) a hypnotic. The composition and method features discussed herein may be used in any combination with embodiments incorporating the hypnotic.

In some embodiments, the methods include administering a dose of 20-100 mg atomoxetine (or a dose equivalent thereof of another NRI), a dose of 2-15 mg (R)-oxybutynin, and a dose of 0.5-15 mg zolpidem (or a dose equivalent thereof of another hypnotic). In some embodiments, the methods include administering 75 mg atomoxetine/6 mg (R)-oxybutynin/10 mg zolpidem; 75 mg atomoxetine/5 mg (R)-oxybutynin/10 mg zolpidem; 75 mg atomoxetine/4.5 mg (R)-oxybutynin/5 mg zolpidem; 50 mg atomoxetine/4 mg (R)-oxybutynin/3.5 mg zolpidem; or 25 mg atomoxetine/3 mg (R)-oxybutynin/1.75 mg zolpidem, e.g., 15-60, e.g., 15-25, 20-30, or 20-45 minutes before sleep time. In some embodiments, the hypnotic is present in an amount of from about 0.5 to about 15 mg, from about 0.5 to about 10 mg, from about 0.5 to about 5 mg, from about 0.5 to about 3.5 mg, or from about 0.5 to about 1.75 mg. In some embodiments, the norepinephrine reuptake inhibitor (NRI), substantially enantiomerically pure (R)-oxybutynin, and hypnotic are administered in a single composition, for example, an oral administration in a syrup, pill, tablet, capsule, or patch form.

Pharmaceutical compositions are typically formulated to be compatible with its intended route of administration. Examples of routes of administration include systemic oral or transdermal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, oral compositions generally include an inert diluent or an edible carrier. For the purpose of oral therapeutic administration, the active compound(s) can be incorporated with excipients and used in the form of pills, tablets, troches, or capsules, e.g., gelatin capsules. Oral compositions can also be prepared using a fluid carrier. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of one or both of the compounds as described herein (i.e., one or both of a norepinephrine reuptake inhibitor and substantially enantiomerically pure (R)-oxybutynin) can also be by transdermal means, e.g., using a patch, gel, or lotion, to be applied to the skin. For transdermal administration, penetrants appropriate to the permeation of the epidermal barrier can be used in the formulation. Such penetrants are generally known in the art. For example, for transdermal administration, the active compounds can formulated into ointments, salves, gels, or creams as generally known in the art. The gel and/or lotion can be provided in individual sachets, or via a metered-dose pump that is applied daily; see, e.g., Cohn et al., Ther Adv Urol. 2016 April; 8(2): 83-90.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration or use in a method described herein.

EXAMPLES

The invention is further described in the following examples, which do not limit the scope of the invention described in the claims.

Example 1. Pilot Study

In healthy human individuals, the effect of the selective noradrenergic reuptake inhibitor, atomoxetine 80 mg, in combination with the antimuscarinic drug (R)-oxybutynin 5 mg on genioglossus muscle activity is measured in a pilot study.

A first group of the patients is given the combination of atomoxetine 80 mg and (R)-oxybutynin 5 mg. A second group of patients is given placebo. Genioglossus muscle activity ($EMG_{GG}$, quantified as a percentage of maximum) is measured during quiet wakefulness. Each peak $EMG_{GG}$ of a single breath is measured and is plotted against the corresponding epiglottic pressure. In addition, $EMG_{GG}$ is measured during stable NREM sleep.

It is expected that there will be a variable but clear reduction in $EMG_{GG}$ activity during sleep on the placebo night and that, in contrast, when patients are administered atomoxetine+(R)-oxybutynin, the sleep-related reduction in pharyngeal muscle activity will be partially or completely prevented.

It is expected that, compared to placebo, the tested drugs will yield a much higher $EMG_{GG}$ activity during NREM sleep. It is also expected that the drugs will be effective during REM sleep for those subjects exhibiting REM sleep when administered the tested drugs.

Example 2. Crossover Study

A placebo-controlled, double-blinded, randomized, crossover trial in OSA human patients is performed. Participants receive treatment (atomoxetine 80 mg+(R)-oxybutynin 5 mg) or placebo in randomized order 30 minutes before sleep. The combination of atomoxetine and (R)-oxybutynin is expected to reduce the apnea hypopnea index and all patients are expected to experience an improvement in OSA severity. Additional benefits expected are increased genioglossus muscle responsiveness to an increase in ventilatory drive, improved upper airway muscle activity, improved ventilation, increased oxygen levels (SaO2), increased total sleep time and improved sleep efficiency.

REFERENCES

1. Young T, Peppard P E, Gottlieb D J. Epidemiology of obstructive sleep apnea: a population health perspective. Am J Respir Crit Care Med 2002; 165:1217-39.
2. Engleman H M, Wild M R. Improving CPAP use by patients with the sleep apnea/hypopnea syndrome (SAHS). Sleep Med Rev 2003; 7:81-99.
3. Kribbs N B, Pack A I, Kline L R, et al. Objective measurement of patterns of nasal CPAP use by patients with obstructive sleep apnea. The American review of respiratory disease 1993; 147:887-95.
4. Chan E, Steenland H W, Liu H, Homer R L. Endogenous excitatory drive modulating respiratory muscle activity across sleep-wake states. American journal of respiratory and critical care medicine 2006; 174:1264-73.
5. Grace K P, Hughes S W, Homer R L. Identification of the mechanism mediating genioglossus muscle suppression in REM sleep. Am J Respir Crit Care Med 2013; 187: 311-9.
6. Kubin L, Davies R O, Pack A I. Control of Upper Airway Motoneurons During REM Sleep. News Physiol Sci 1998; 13:91-7.
7. Sood S, Morrison J L, Liu H, Horner R L. Role of endogenous serotonin in modulating genioglossus muscle activity in awake and sleeping rats. American journal of respiratory and critical care medicine 2005; 172:1338-47.
8. Sood S, Raddatz E, Liu X, Liu H, Homer R L. Inhibition of serotonergic medullary raphe obscurus neurons suppresses genioglossus and diaphragm activities in anesthetized but not conscious rats. J Appl Physiol (1985) 2006; 100:1807-21.
9. Fenik V B, Davies R O, Kubin L. REM sleep-like atonia of hypoglossal (XII) motoneurons is caused by loss of noradrenergic and serotonergic inputs. Am J Respir Crit Care Med 2005; 172:1322-30.
10. Sood S, Liu X, Liu H, Homer R L. Genioglossus muscle activity and serotonergic modulation of hypoglossal motor output in obese Zucker rats. J Appl Physiol (1985) 2007; 102:2240-50.
11. Hanzel D A, Proia N G, Hudgel D W. Response of obstructive sleep apnea to fluoxetine and protriptyline. Chest 1991; 100:416-21.
12. Kraiczi H, Hedner J, Dahlof P, Ejnell H, Carlson J. Effect of serotonin uptake inhibition on breathing during sleep and daytime symptoms in obstructive sleep apnea. Sleep 1999; 22:61-7.
13. Berry R B, Yamaura E M, Gill K, Reist C. Acute effects of paroxetine on genioglossus activity in obstructive sleep apnea. Sleep 1999; 22:1087-92.
14. Lai Y Y, Kodama T, Siegel J M. Changes in monoamine release in the ventral horn and hypoglossal nucleus linked to pontine inhibition of muscle tone: an in vivo microdialysis study. J Neurosci 2001; 21:7384-91.
15. Grace K P, Hughes S W, Shahabi S, Horner R L. K+ channel modulation causes genioglossus inhibition in REM sleep and is a strategy for reactivation. Respir Physiol Neurobiol 2013; 188:277-88.
16. Eckert D J, White D P, Jordan A S, Malhotra A, Wellman A. Defining phenotypic causes of obstructive sleep apnea. Identification of novel therapeutic targets. Am J Respir Crit Care Med 2013; 188:996-1004.
17. Wellman A, Eckert D J, Jordan A S, Edwards B A, Passaglia C L, Jackson A C, Gautam S, Owens R L, Malhotra A, White D P. A method for measuring and modeling the physiological traits causing obstructive sleep apnea. J Appl Physiol 2011; 110:1627-1637.
18. Wellman A, Edwards B A, Sands S A, Owens R L, Nemati S, Butler J P, Passaglia C L, Jackson A C, Malhotra A, White D P. A simplified method for determining phenotypic traits in patients with obstructive sleep apnea. J Appl Physiol 2013.
19. Younes M. Contributions of upper airway mechanics and control mechanisms to severity of obstructive apnea. Am J Respir Crit Care Med 2003; 168:645-658.
20. Somers V K, Dyken M E, Clary M P, Abboud F M. Sympathetic neural mechanisms in obstructive sleep apnea. J Clin Invest 1995; 96:1897-1904.
21. Nieto F J, Young T B, Lind B K, Shahar E, Samet J M, Redline S, D'Agostino R B, Newman A B, Lebowitz M D, Pickering T G. Association of sleep-disordered breathing, sleep apnea, and hypertension in a large community-based study. Sleep heart health study. Jama 2000; 283: 1829-1836.
22. Brooks D, Homer R L, Kozar L F, Render-Teixeira C L, Phillipson E A. Obstructive sleep apnea as a cause of systemic hypertension. Evidence from a canine model. J Clin Invest 1997; 99:106-109.
23. Peppard P E, Young T, Palta M, Skatrud J. Prospective study of the association between sleep-disordered breathing and hypertension. The New England journal of medicine 2000; 342:1378-1384.
24. Hung J, Whitford E G, Parsons R W, Hillman D R. Association of sleep apnea with myocardial infarction in men. Lancet 1990; 336:261-264.
25. Wessendorf T E, Teschler H, Wang Y M, Konietzko N, Thilmann A F. Sleep-disordered breathing among patients with first-ever stroke. J Neurol 2000; 247:41-47.
26. Hoffstein V. Blood pressure, snoring, obesity, and nocturnal hypoxaemia. Lancet 1994; 344:643-645.
27. Shahar E, Whitney C W, Redline S, Lee E T, Newman A B, Nieto F J, O'Connor G T, Boland L L, Schwartz J E, Samet J M. Sleep-disordered breathing and cardiovascular disease: Cross-sectional results of the sleep heart health study. Am J Respir Crit Care Med 2001; 163:19-25.
28. Redline S, Strauss M E, Adams N, Winters M, Roebuck T, Spry K, Rosenberg C, Adams K. Neuropsychological function in mild sleep-disordered breathing. Sleep 1997; 20:160-167.
29. Findley L I, Unverzagt M E, Suratt P M. Automobile accidents involving patients with obstructive sleep apnea. Am Rev Respir Dis 1988; 138:337-340.
30. Edwards B A, Sands S A, Eckert D J, White D P, Butler J P, Owens R L, Malhotra A, Wellman A. Acetazolamide improves loop gain but not the other physiological traits causing obstructive sleep apnoea. J Physiol 2012; 590: 1199-1211.
31. Wellman A, Malhotra A, Jordan A S, Stevenson K E, Gautam S, White D P. Effect of oxygen in obstructive sleep apnea: Role of loop gain. Respir Physiol Neurobiol 2008; 162:144-151.
32. Lai Y Y, Kodama T, Siegel J M. Changes in monoamine release in the ventral horn and hypoglossal nucleus linked to pontine inhibition of muscle tone: An in vivo microdialysis study. J Neurosci 2001; 21:7384-7391.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a condition associated with pharyngeal airway collapse, the method comprising administering to a subject in need thereof an effective amount of a combination of (i) Atomoxetine and (ii) substantially enantiomerically pure (R)-oxybutynin, wherein the enantiomeric excess of the (R)-oxybutynin relative to its opposite enantiomer is greater than or equal to 90%.

2. The method of claim 1, wherein the Atomoxetine is administered at a dosage of from about 20 to about 100 mg.

3. The method of claim 1, wherein the (R)-oxybutynin is administered at a dosage of from about 2 to about 15 mg.

4. The method of claim 1, wherein the condition associated with pharyngeal airway collapse is Sleep Apnea or Simple Snoring.

5. The method of claim 1, wherein the condition associated with pharyngeal airway collapse is Obstructive Sleep Apnea (OSA).

6. The method of claim 1, wherein the subject is in a non-fully conscious state, wherein the non-fully conscious state is sleep.

7. The method of claim 1, wherein the Atomoxetine and (R)-oxybutynin are administered in a single composition, wherein the single composition is an oral administration form.

8. A method of treating obstructive sleep apnea in a subject in need thereof, the method comprising administering to the subject an effective amount of a combination of (i) Atomoxetine and (ii) substantially enantiomerically pure (R)-oxybutynin, wherein the enantiomeric excess of the (R)-oxybutynin relative to its opposite enantiomer is greater than or equal to 90%.

9. The method of claim 8, wherein the Atomoxetine is administered at a dosage of from about 20 to about 100 mg and the (R)-oxybutynin is administered at a dosage of from about 2 to about 15 mg.

10. The method of claim 8, wherein the subject is in a non-fully conscious state, wherein the non-fully conscious state is sleep.

11. The method of claim 8, wherein the Atomoxetine and (R)-oxybutynin are administered in a single composition, wherein the single composition is an oral administration form.

12. A method of treating obstructive sleep apnea in a subject in need thereof, the method comprising decreasing an apnea-hypopnea index (AHI) of the subject by generating a circulating concentration of Atomoxetine and substantially enantiomerically pure (R)-oxybutynin in the subject that results in a decrease in AHI, wherein the enantiomeric excess of the (R)-oxybutynin relative to its opposite enantiomer is greater than or equal to 90%.

13. A method of treating obstructive sleep apnea in a subject in need thereof, the method comprising administering to the subject a pharmaceutical composition comprising:

a first active ingredient, a second active ingredient, and one or more pharmaceutically acceptable excipients; wherein the first active ingredient comprises Atomoxetine and the second active ingredient comprises (R)-oxybutynin, and wherein the (R)-oxybutynin is substantially enantiomerically pure and the enantiomeric excess of the (R)-oxybutynin relative to its opposite enantiomer is greater than or equal to 90%.

14. The method of claim 1, wherein the enantiomeric excess of the (R)-oxybutynin relative to its opposite enantiomer is greater than or equal to 95%.

15. The method of claim 8, wherein the enantiomeric excess of the (R)-oxybutynin relative to its opposite enantiomer is greater than or equal to 95%.

16. The method of claim 12, wherein the enantiomeric excess of the (R)-oxybutynin relative to its opposite enantiomer is greater than or equal to 95%.

17. The method of claim 13, wherein the enantiomeric excess of the (R)-oxybutynin relative to its opposite enantiomer is greater than or equal to 95%.

18. The method of claim 1, wherein the enantiomeric excess of the (R)-oxybutynin relative to its opposite enantiomer is greater than or equal to 98%.

19. The method of claim 8, wherein the enantiomeric excess of the (R)-oxybutynin relative to its opposite enantiomer is greater than or equal to 98%.

20. The method of claim 12, wherein the enantiomeric excess of the (R)-oxybutynin relative to its opposite enantiomer is greater than or equal to 98%.

21. The method of claim 13, wherein the enantiomeric excess of the (R)-oxybutynin relative to its opposite enantiomer is greater than or equal to 98%.

22. The method of claim 1, wherein the enantiomeric excess of the (R)-oxybutynin relative to its opposite enantiomer is greater than or equal to 99%.

23. The method of claim 8, wherein the enantiomeric excess of the (R)-oxybutynin relative to its opposite enantiomer is greater than or equal to 99%.

24. The method of claim 12, wherein the enantiomeric excess of the (R)-oxybutynin relative to its opposite enantiomer is greater than or equal to 99%.

25. The method of claim 13, wherein the enantiomeric excess of the (R)-oxybutynin relative to its opposite enantiomer is greater than or equal to 99%.

* * * * *